United States Patent
Gillespie et al.

(10) Patent No.: US 11,992,566 B2
(45) Date of Patent: May 28, 2024

(54) SELF SANITIZING STORAGE OF A DELIVERY ROBOT

(71) Applicant: Serve Robotics Inc., Redwood City, CA (US)

(72) Inventors: David Gillespie, Los Angeles, CA (US); Colin Janssen, Vancouver (CA); Sean Plaice, San Francisco, CA (US); Aaron Leiba, Los Angeles, CA (US); Ali Haghighat Kashani, San Francisco, CA (US)

(73) Assignee: Serve Robotics Inc., Redwood City, CA (US)

( * ) Notice: Subject to any disclaimer, the term of this patent is extended or adjusted under 35 U.S.C. 154(b) by 461 days.

(21) Appl. No.: 17/249,985

(22) Filed: Mar. 19, 2021

(65) Prior Publication Data
US 2021/0290796 A1   Sep. 23, 2021

Related U.S. Application Data

(60) Provisional application No. 62/992,878, filed on Mar. 20, 2020.

(51) Int. Cl.
| | |
|---|---|
| *A61L 2/10* | (2006.01) |
| *A61L 2/20* | (2006.01) |
| *A61L 2/24* | (2006.01) |
| *A61L 2/26* | (2006.01) |

(52) U.S. Cl.
CPC ............ *A61L 2/10* (2013.01); *A61L 2/202* (2013.01); *A61L 2/24* (2013.01); *A61L 2/26* (2013.01); *A61L 2202/11* (2013.01); *A61L 2202/121* (2013.01); *A61L 2202/122* (2013.01); *A61L 2202/14* (2013.01); *A61L 2202/15* (2013.01)

(58) Field of Classification Search
CPC ... A61L 2/10; A61L 2/202; A61L 2/24; A61L 2/26; A61L 2202/11; A61L 2202/121; A61L 2202/122; A61L 2202/14; A61L 2202/15; A61L 2202/16
See application file for complete search history.

(56) References Cited

U.S. PATENT DOCUMENTS

| | | | |
|---|---|---|---|
| 10,894,100 B2 * | 1/2021 | Georgeson | ................ A61L 2/10 |
| 2006/0147339 A1 * | 7/2006 | Hunter | ...................... A61L 2/10 |
| | | | 250/455.11 |

(Continued)

FOREIGN PATENT DOCUMENTS

| | | | | |
|---|---|---|---|---|
| CN | 109202939 A | * | 1/2019 | |
| CN | 106363645 B | * | 3/2019 | ............. A61G 12/00 |

*Primary Examiner* — Jennifer Wecker
*Assistant Examiner* — Brady C Pilsbury
(74) *Attorney, Agent, or Firm* — Weaver Austin Villeneuve & Sampson LLP

(57) ABSTRACT

A delivery robot includes a cargo bin to carry cargo for delivery, and a door coupled to the cargo bin. The door to the cargo bin has an open state to allow access to an interior of the cargo bin, and a closed state to seal the interior of the cargo bin from an exterior environment. The delivery robot also includes a disinfecting light source operable to generate a disinfecting radiation to disinfect the interior of the cargo bin. The disinfecting light source is allowed to be activated when the door is in the closed state, and is prevented from being activated when the door is in the open state.

18 Claims, 8 Drawing Sheets

(56) References Cited

U.S. PATENT DOCUMENTS

| | | | |
|---|---|---|---|
| 2013/0004367 A1* | 1/2013 | Roberts | A61L 2/10 |
| | | | 250/504 R |
| 2018/0300676 A1* | 10/2018 | Peterson | B60Q 1/507 |
| 2019/0034857 A1* | 1/2019 | Ferguson | G07F 17/12 |
| 2019/0167827 A1* | 6/2019 | Gaska | A61L 2/10 |
| 2019/0362295 A1* | 11/2019 | Kanitz | B60S 1/64 |
| 2020/0167722 A1* | 5/2020 | Goldberg | G06Q 10/0832 |
| 2021/0097481 A1* | 4/2021 | Salter | A61L 2/088 |
| 2021/0228752 A1* | 7/2021 | Chang | A61L 2/06 |
| 2021/0295242 A1* | 9/2021 | Rathi | G06Q 10/083 |
| 2021/0308300 A1* | 10/2021 | Rathi | A61L 2/04 |
| 2022/0111090 A1* | 4/2022 | Kea | A61L 2/24 |

\* cited by examiner

SELF SANITIZING STORAGE OF A DELIVERY ROBOT

CROSS-REFERENCE TO RELATED APPLICATIONS

The present application is a non-provisional patent application of U.S. Provisional Application No. 62/992,878, which is incorporated by reference in its entirety for all purposes.

BACKGROUND

Robots that operate in an environment where transmission of bacteria and viruses is a concern may need a way to disinfect components that are exposed to human interactions. For example, a delivery robot may need a way to disinfect a cargo holding compartment where different users may place and remove cargo items. Although a user can manually clean the cargo holding compartment, a delivery robot may encounter several different users during a delivery trip, and there is no guarantee that every user would responsibly disinfect the cargo holding compartment after each stop.

BRIEF SUMMARY

A delivery robot may include a cargo bin and a door coupled to the cargo bin. The door to the cargo bin can have an open state to allow access to an interior of the cargo bin, and a closed state to seal the interior of the cargo bin from an exterior environment. The delivery robot may also include a disinfecting light source operable to generate a disinfecting radiation to disinfect the interior of the cargo bin. The disinfecting light source can be allowed to be activated when the door is in the closed state, and can be prevented from being activated when the door is in the open state.

A method for operating a disinfecting light source of a delivery robot may include initiating a delivery robot having a cargo bin to traverse a delivery route to a destination, activating a disinfecting light source integrated with the delivery robot for a first duration of time to disinfect an interior of the cargo bin prior to arriving at the destination, and determining that the delivery robot has arrived at the destination. In response to determining that the delivery robot has arrived at the destination, the disinfecting light source can be deactivated while the delivery robot is stopped at the destination. When the delivery robot is determined to have departed the destination, the disinfecting light source can be reactivated to disinfect the interior of the cargo bin for a second duration of time.

BRIEF DESCRIPTION OF THE DRAWINGS

Various embodiments in accordance with the present disclosure will be described with reference to the drawings.

DETAILED DESCRIPTION

The techniques disclosed herein provide a self-sanitizing storage container. According to various implementations, the storage container can be provided on a delivery vehicle, such as a delivery robot. The storage container can be an integral part of the delivery robot. For example, the storage container can be implemented as a cargo bin integrated with a housing of the robot mounted on a mobile platform (e.g., set of wheels) of the robot. A disinfecting light source (e.g., an ultraviolet (UV) light source) can be coupled to the cargo bin to generate a disinfecting radiation to disinfect the interior of the cargo bin. The disinfecting light source may also disinfect the cargo being transported in the cargo bin. In some implementations, the cargo can be provided with packaging that can block out the radiation of the disinfecting light source, and the disinfecting light source may disinfect the packaging (e.g., the exterior surface of the cargo) without penetrating through the packaging. In other implementations, the radiation emitted from the disinfecting light source may penetrate through the cargo packaging and thereby disinfect the contents of the packaging as well as the packaging.

Figure 1:
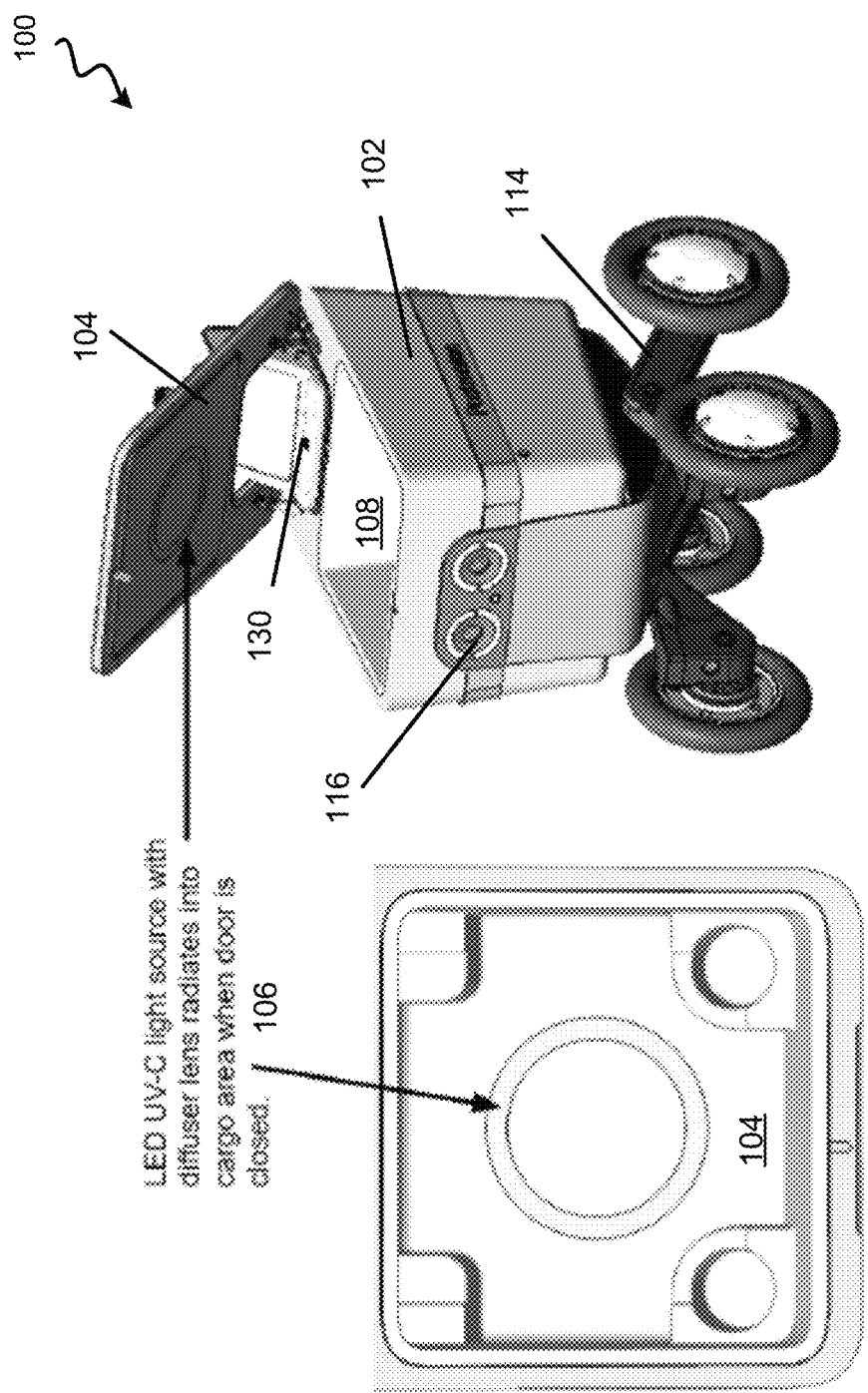
FIG. 1 illustrates a delivery robot with a door in the open state, according to some embodiments.
Figure 2:
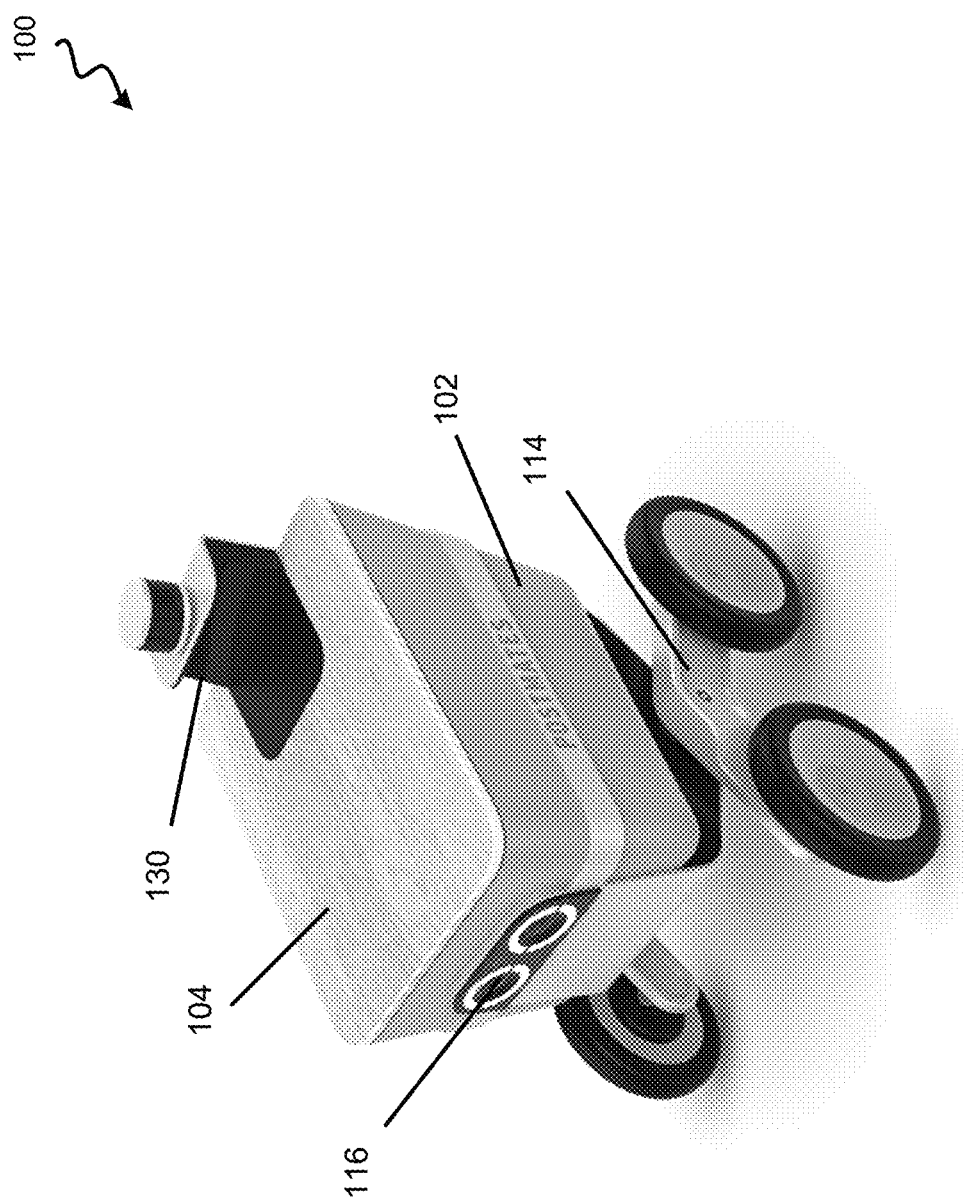
FIG. 2 illustrates a delivery robot with a door in the closed state, according to some embodiments.

FIGS. 1-2 illustrate an example of a delivery robot 100, according to some implementations. Delivery robot 100 can be used, for example, to deliver merchandise from a merchant to a consumer, a meal from a restaurant to a customer, medication from a pharmacy to a patient, or other items suitable for delivery. Delivery robot 100 includes a housing 102 provided on a mobile platform 114 implemented as a set of wheels. Delivery robot 100 also includes a controller 130 which can be part of a control unit with a display. In some implementations, controller 130 can be located elsewhere in delivery robot 100. Delivery robot 100 may also include exterior lighting 116 to increase the visibility of delivery robot 100 in low light conditions and to provide various icons or patterns to indicate a state of delivery robot (e.g., moving, stopped, etc.).

The housing 102 may include a cargo bin 108 that can be accessed via a door 104. Door 104 can have an open state as illustrated in FIG. 1 to allow access to an interior of cargo bin 108, and a closed state as illustrated in FIG. 2 to seal the interior of cargo bin 108 from an exterior environment. In some implementations, in order to open door 104, a user may be required to provide authentication information to control unit 130. The authentication information can be, for example, a numeric or alphanumeric code, a bar code, a QR code, or other identifying information. In the example shown in FIG. 1, door 104 is arranged on a topside of cargo bin 108. However, it should be understood that door 104 can be arranged on a different part of cargo bin 108 such as on the side, front, or back of cargo bin 108.

Delivery robot 100 may also include a disinfecting light source 106 operable to generate a disinfecting radiation to disinfect the interior of the cargo bin 108. Disinfecting light source 106 can be an onboard light source coupled to or integrated with door 104. For example, disinfecting light source 106 can be arranged on the inside surface of door 104. In some implementations, disinfecting light source 106 can be flushed with the inside surface of door 104, or may protrude from the surface of door 104. The particular configuration shown in FIG. 1 in which door 104 is arranged on the topside of cargo bin 108 and the disinfecting light source 106 arranged on the inside of door 104 may allow the radiation generated by disinfecting light source 106 to cover as much of the cargo compartment as possible. However, it should be understood that it is not necessary for disinfecting light source 106 to be integrated with door 104, and that disinfecting light source 106 can be arranged elsewhere, such as on a side surface of the interior of cargo bin 108.

Disinfecting light source 106 can be activated to emit disinfecting radiation (e.g., ultraviolet (UV) light) to disinfect cargo bin 108 as well as the cargo provided therein. In some implementations, disinfecting light source 106 may include one or more short-wavelength ultraviolet (UV-C) light sources to disinfect as much surface area as possible using ultraviolet germicidal irradiation (UVGI). Various types of UV light sources can be used such as light emitting diodes (LEDs), high pressure lamps, low pressure lamps, or any combination thereof. In some implementations, the emitted disinfecting radiation (e.g., UV light emitted from LEDs) can be diffused using lenses to increase the coverage area. Transmissive and reflective optics could be placed inside cargo bin 108 to shape the light beam, as well for materials or coatings used in cargo bin 108 to redirect the light to areas that may be hidden or hard to reach from the location of disinfecting light source 106. For example, the interior surface 108 of the cargo bin 102 may be lined (or coated) partially or in its entirety with a reflective material or reflective optics to form a reflective surface to reflect the disinfecting radiation toward a portion of the interior of cargo bin 108. The interior of cargo bin 108 may also include a transmissive surface such as a waveguide to transmit or direct the disinfecting radiation toward a portion of the interior of cargo bin 108.

In some implementations, disinfecting light source 106 may include an ozone creating vacuum-UV light source that can generate small amounts of ozone to disinfect areas that the UV-C light cannot reach. In such implementations, delivery robot 100 may also include a fan operable to circulate the ozone in cargo bin 108. The fan can be activated and deactivated at the same time as disinfecting light source 106, or remain activated after disinfecting light source 106 has been turned off to continue circulating the ozone. In some implementations, the ozone creating vacuum-UV light source can be used in combination with other UV light sources.

During operation, disinfecting light source 106 can be allowed to be activated when door 104 is in the closed state, and be prevented from being activated when door 104 is in the open state. This can effectively provide a safety feature to prevent disinfecting light source 106 from irradiating an unintended target such as a user opening door 104. For example, door 104 may include electrical contacts that establishes an electrical connection to provide power to disinfecting light source 106 when door 104 is closed, but disconnects disinfecting light source 106 from the power source when door 104 is open. Controller 130 can also be programmed to control the power to disinfecting light source 106 based on the detected state of door 104. In some implementations, the display of the control unit and/or the exterior lighting 116 may provide an indicator indicating whether disinfecting light source 106 is activated or deactivated.

When delivery robot 100 is in use making deliveries, delivery robot 100 may activate disinfecting light source 106 before and/or after every interaction with a person. For example, the delivery robot 100 may activate disinfecting light source 106 every time after door 104 of the cargo bin 108 is closed. In some implementations, delivery robot 100 may activate disinfecting light source 106 (instead of or in addition to the closing door 104) for a predetermined amount of time (e.g., 1 min, 5 min, etc.) prior to arriving at a destination. The duration of time that disinfecting light source 106 is activated may depend on a variety of factors including but not limited to the intensity of the disinfecting light source 106, a volume or size of the cargo being delivered, a volume or size of cargo bin 108, a surface area to be disinfected, the exterior temperature, temperature or humidity restrictions associated with the cargo (if any), remaining battery of delivery robot 100, etc. In some implementations, the duration of time that disinfecting light source 106 is activated can depend on whether delivery robot 100 is arriving/departing a pickup location or a drop-off location. Furthermore, a disinfection cycle can be performed daily or when delivery robot 100 returns to its base station.

Figure 3:
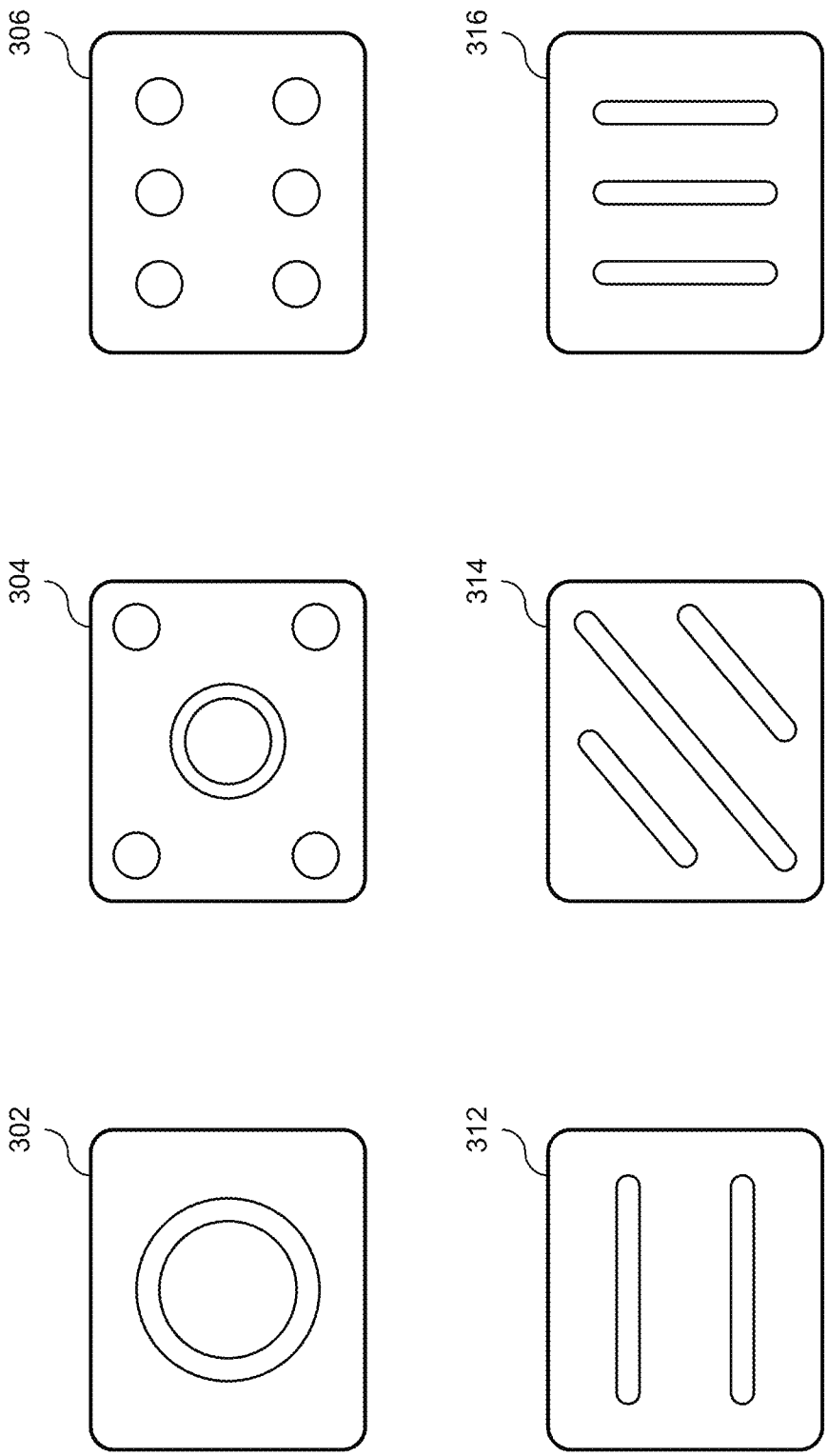
FIG. 3 illustrates various configurations of a disinfecting light source, according to some embodiments.

FIG. 3 illustrates various implementations of a disinfecting light source. The disinfecting light source can be mounted or be integrated with a surface such as a door or lid of a cargo bin, or on a side of a cargo bin. Implementation 302 is similar to FIG. 1 in that the disinfecting light source has a ring shape that spans greater than half the width of the surface and is arranged in the middle of the surface. Implementation 304 includes a smaller ring-shaped disinfecting light source arranged in the middle of the surface as well as four smaller circular-shaped disinfecting light sources arranged proximate to the corners of the surface. Implementation 306 includes an array of circular-shaped disinfecting light sources. Implementation 312 includes multiple linear-shaped disinfecting light sources arranged horizontally on the surface. Implementation 314 includes multiple linear-shaped disinfecting light sources arranged diagonally on the surface. Implementation 316 includes multiple linear-shaped disinfecting light sources arranged vertically on the surface. It should be understood that these are just examples, and the disinfecting light sources of the delivery robot may include one or more sources in any various combination of shapes and sizes.

Figure 4:
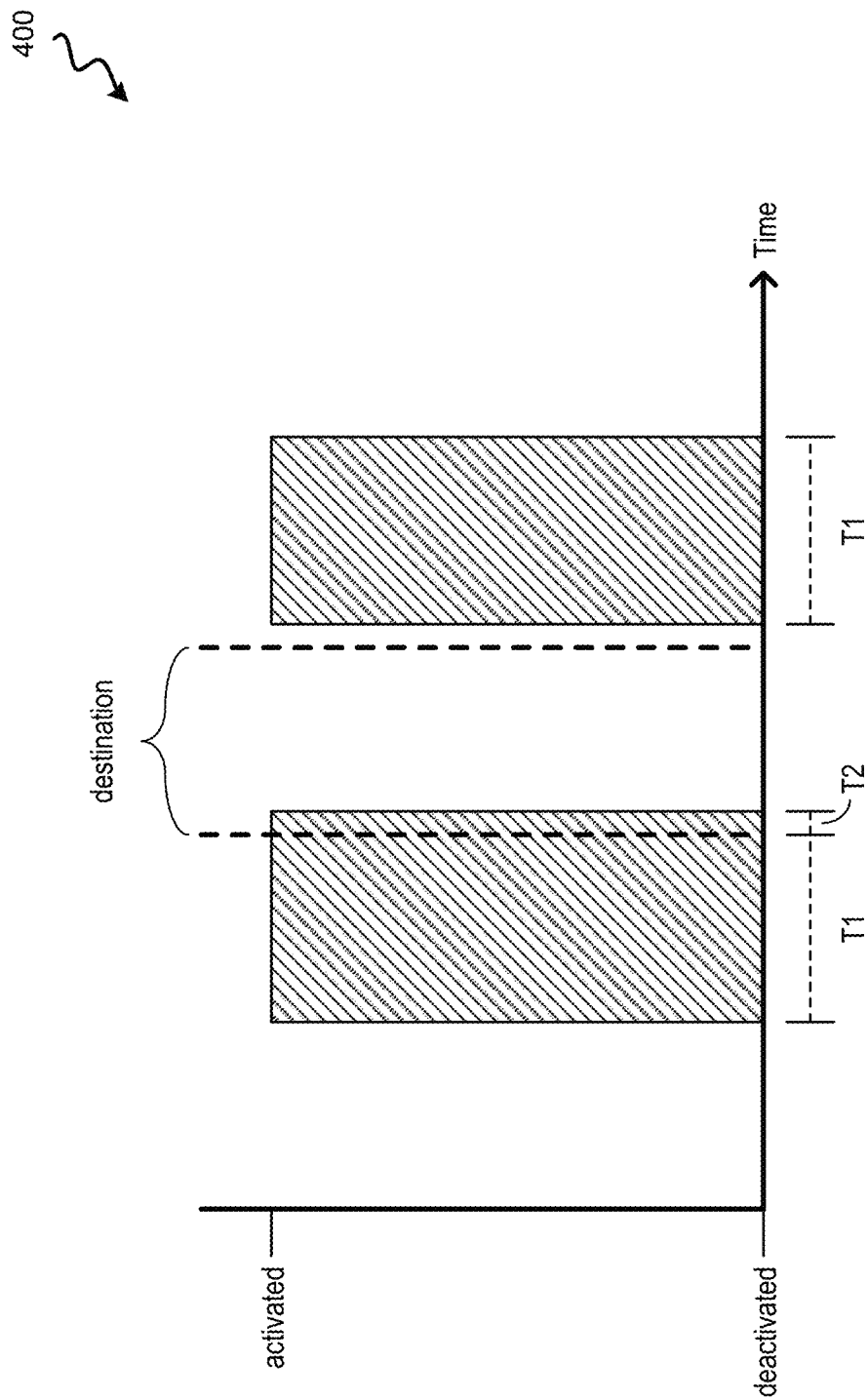
FIG. 4 illustrates a timing diagram of activating a disinfecting light source, according to some embodiments.

FIG. 4 illustrates a timing diagram 400 of an example of the relative durations that a delivery robot activates the disinfecting light source. The shaded region shown in FIG. 4 corresponds to the disinfecting light source being activated. It is assumed that the disinfecting light source is activated while the door to the cargo bin is closed. The activation and deactivation of the disinfecting light source can be performed, for example, by a controller of the delivery robot. The delivery robot can be programmed to navigate a delivery route to a destination. Before arriving at the destination, the disinfecting light source can be activated for a first duration of time T1. For example, the disinfecting light source can be activated when the estimated time-of-arrival determined from a navigation system of the delivery robot corresponds to the time T1. Time T1 can be, for example, 5 minutes, 10 minutes, etc.

In some implementations, the disinfecting light source is kept activated for a second duration of time T2 once the delivery robot has arrived at the destination. Time T2 can be significantly less than time T1. For example, time T2 can be 5 seconds, 10 seconds, 20 seconds, etc. Disinfecting light source can be kept activated when the delivery robot has arrived at the destination to indicate to a user that the cargo bin of the delivery robot has been sanitized or cleaned.

While the delivery robot is at the destination, a user may open the door to the cargo bin to place item(s) therein for delivery to another user, or remove item(s) form the cargo bin being delivered to the user. After the delivery robot has departed the destination, the disinfecting light source can be reactivated for another duration of time (e.g., time T1).

Figure 5:
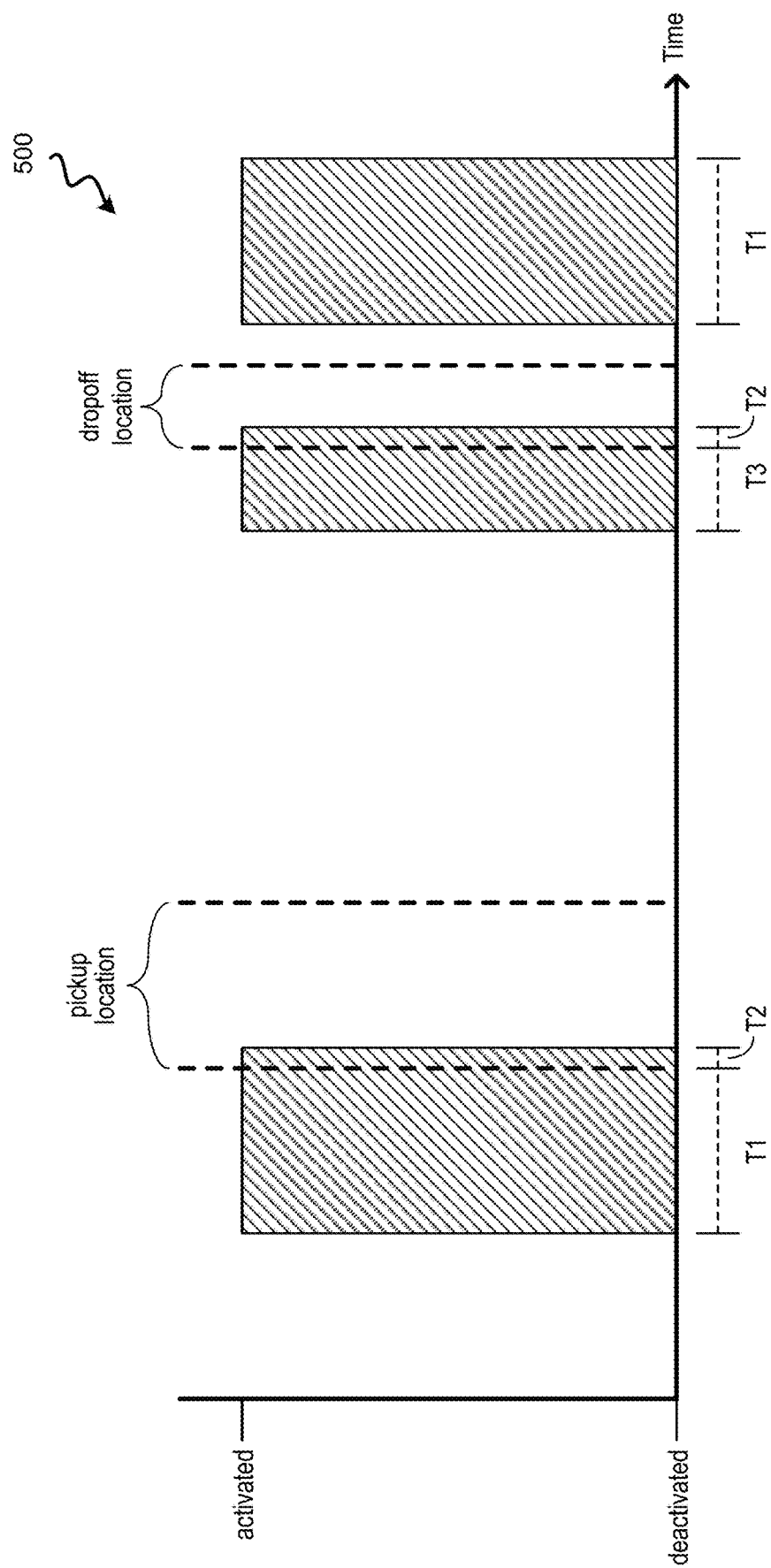
FIG. 5 illustrates another timing diagram of activating a disinfecting light source, according to some embodiments.

FIG. 5 illustrates a timing diagram 500 of another example of the relative durations that a delivery robot activates the disinfecting light source. In timing diagram 500, the duration of time that the disinfecting light source is activated can be varied based on whether the destination is a pickup location or a drop-off location. Prior to arriving to a pickup location, the cargo bin may be empty, and the disinfecting light source can be activated for a duration of time T1. Similar to timing diagram 400, the disinfecting light source is kept activated for a second duration of time T2 once the delivery robot has arrived at the pickup location to indicate to a user that the cargo bin has been cleaned. While the delivery robot is at the pickup location, a user may place item(s) in the cargo bin for delivery to a drop-off location.

In some implementations, the disinfecting light source is not activated as the delivery robot is departing the pickup location because the disinfecting light source will be activated when the delivery robot gets closer to the drop-off location. Prior to arriving to the drop-off location, the disinfecting light source can be activated for a duration of time T3. The duration of time T3 can be less than the duration of time T1 because the cargo bin is carrying cargo at this time, and it may be undesirable to expose that cargo to an extended period of UV light. Similar to above, the disinfecting light source is kept activated for a second duration of time T2 once the delivery robot has arrived at the drop-off location to indicate to the recipient that the cargo bin has been cleaned. While at the drop-off location, the recipient may remove the item(s) being delivered. After the delivery robot has departed the drop-off location, the disinfecting light source can be reactivated for another duration of time T1.

Figure 6:
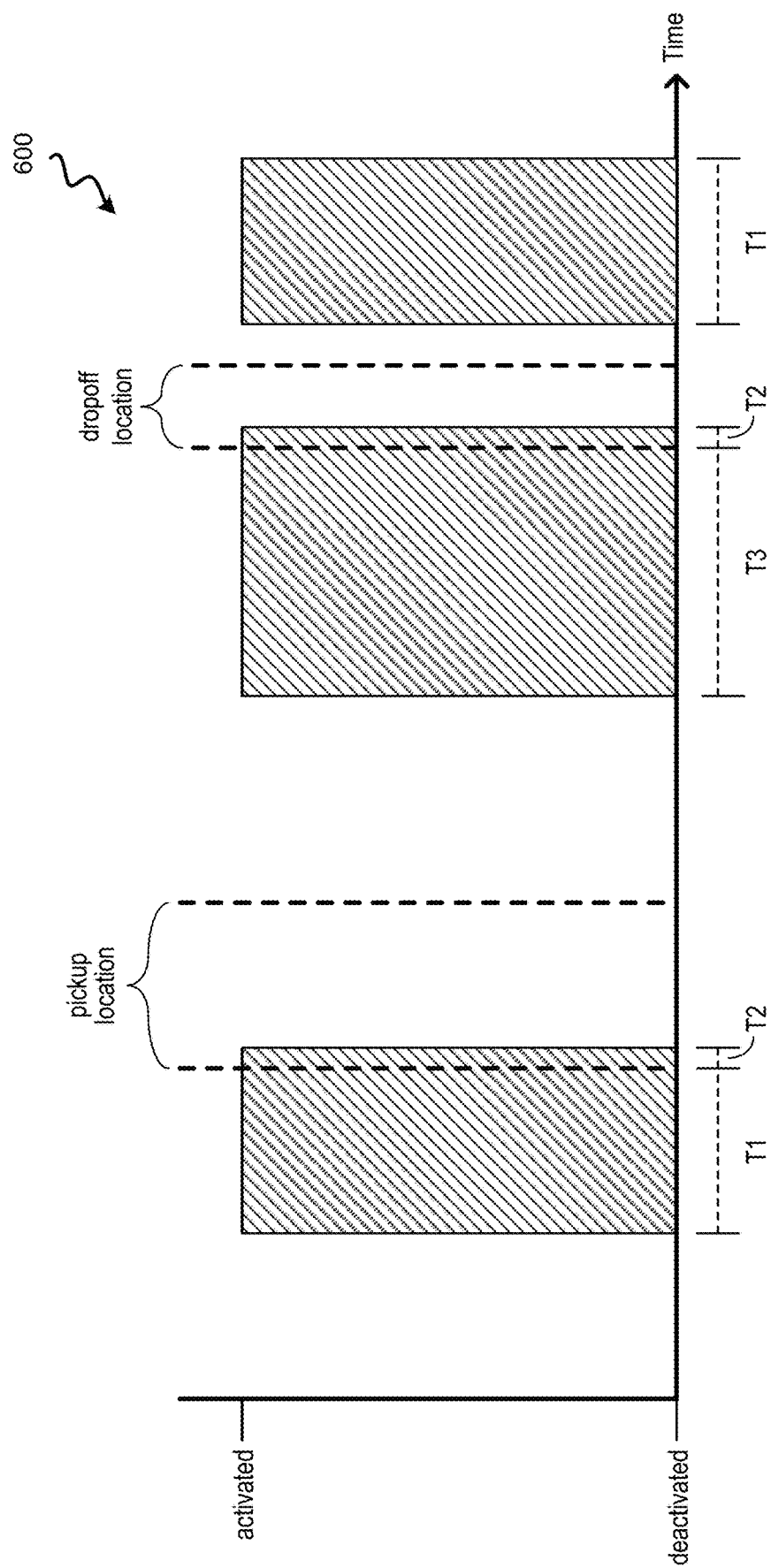
FIG. 6 illustrates a further timing diagram of activating a disinfecting light source, according to some embodiments.

FIG. 6 illustrates a timing diagram 600 of another example of the relative durations that a delivery robot activates the disinfecting light source. Timing diagram 600 is similar to that of timing diagram 500, except the duration of time T3 that the disinfecting light source is activated before arriving at the drop-off location is longer than the duration of time T1. In this example, it may be desirable to disinfect the cargo that is being delivered. As such, the disinfecting light source can be activated for a longer period of time to sanitize the cargo being delivered.

It should be understood that the timing diagrams described above are just examples, and that the disinfecting light source can be activated and deactivated at different times and durations. For example, the disinfecting light source can be activated multiple times between destinations. As another example, the disinfecting light source can be activated for a predetermined duration of time each time that the door of the cargo bin is closed, or may remain activated as long as the door is closed while on a delivery route.

Figure 7:
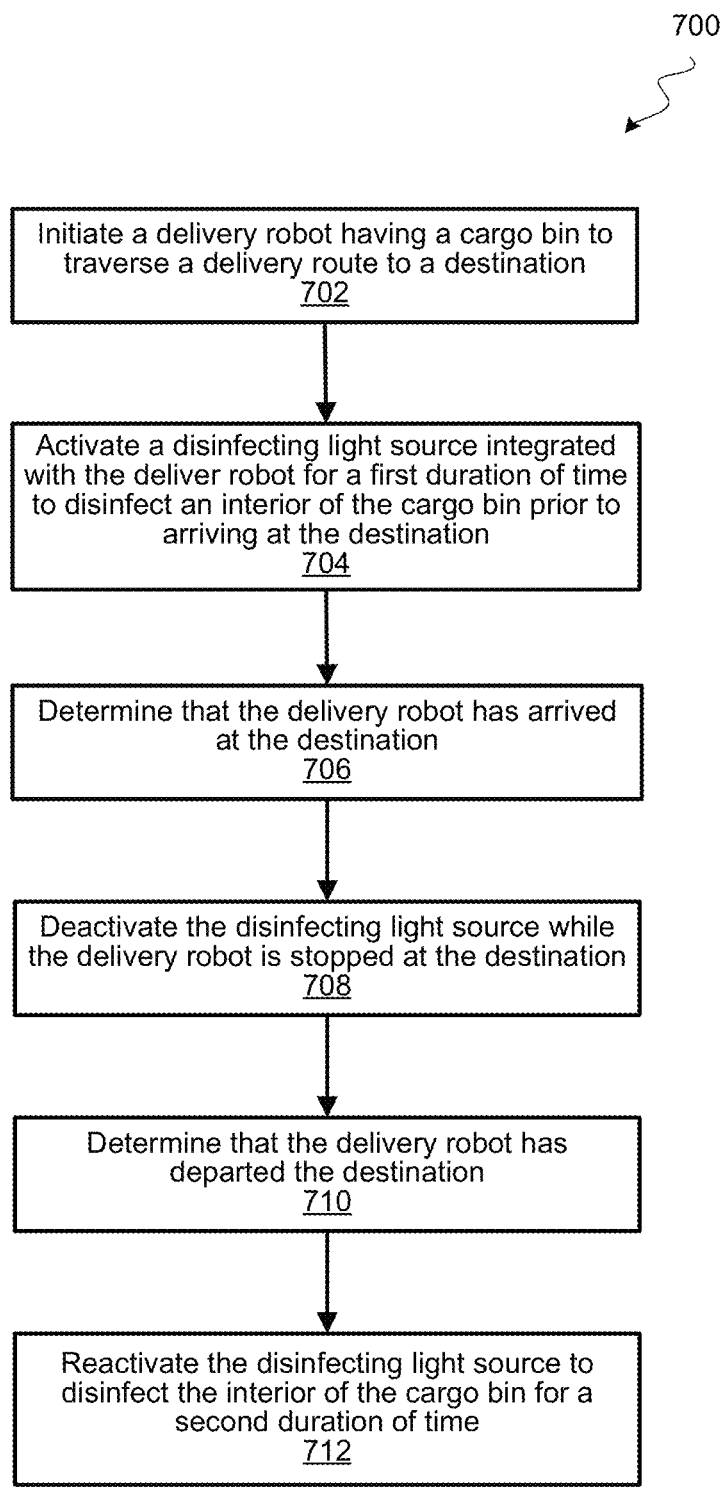
FIG. 7 illustrates a flow diagram of a process for activating a disinfecting light source, according to some embodiments.

FIG. 7 illustrates a flow diagram of a process 700 for operating a disinfecting light source of a delivery robot, according to some embodiments. Process 700 may begin at block 702 by initiating a delivery robot having a cargo bin to traverse a delivery route to a destination. At block 704, a disinfecting light source integrated with the delivery robot can be activated for a first duration of time to disinfect an interior of the cargo bin prior to arriving at the destination. At block 706, the delivery robot is determined to have arrived at the destination (e.g., based on GPS data). At block 708, in response to determining that the delivery robot has arrived at the destination, the disinfecting light source is deactivated while the delivery robot is stopped at the destination. At block 710, the delivery robot is determined to have departed the destination. At block 712, in response to determining that the delivery robot has departed the destination, the disinfecting light source is reactivated to disinfect the interior of the cargo bin for a second duration of time.

In some embodiments, the destination can be a cargo pickup location, and the second duration of time can be shorter than the first duration of time to prevent exposing the cargo to UV light for an extended period of time. Alternatively, the second duration of time can be longer than the first duration of time to disinfect the cargo being delivered. In some embodiments, the destination can be a cargo drop-off location, and the second duration of time can be shorter than the first duration of time, or the second duration of time can be longer than the first duration of time. In other embodiments, the first and second durations of time that the disinfecting light source is activated before and after a destination can be the same.

Figure 8:
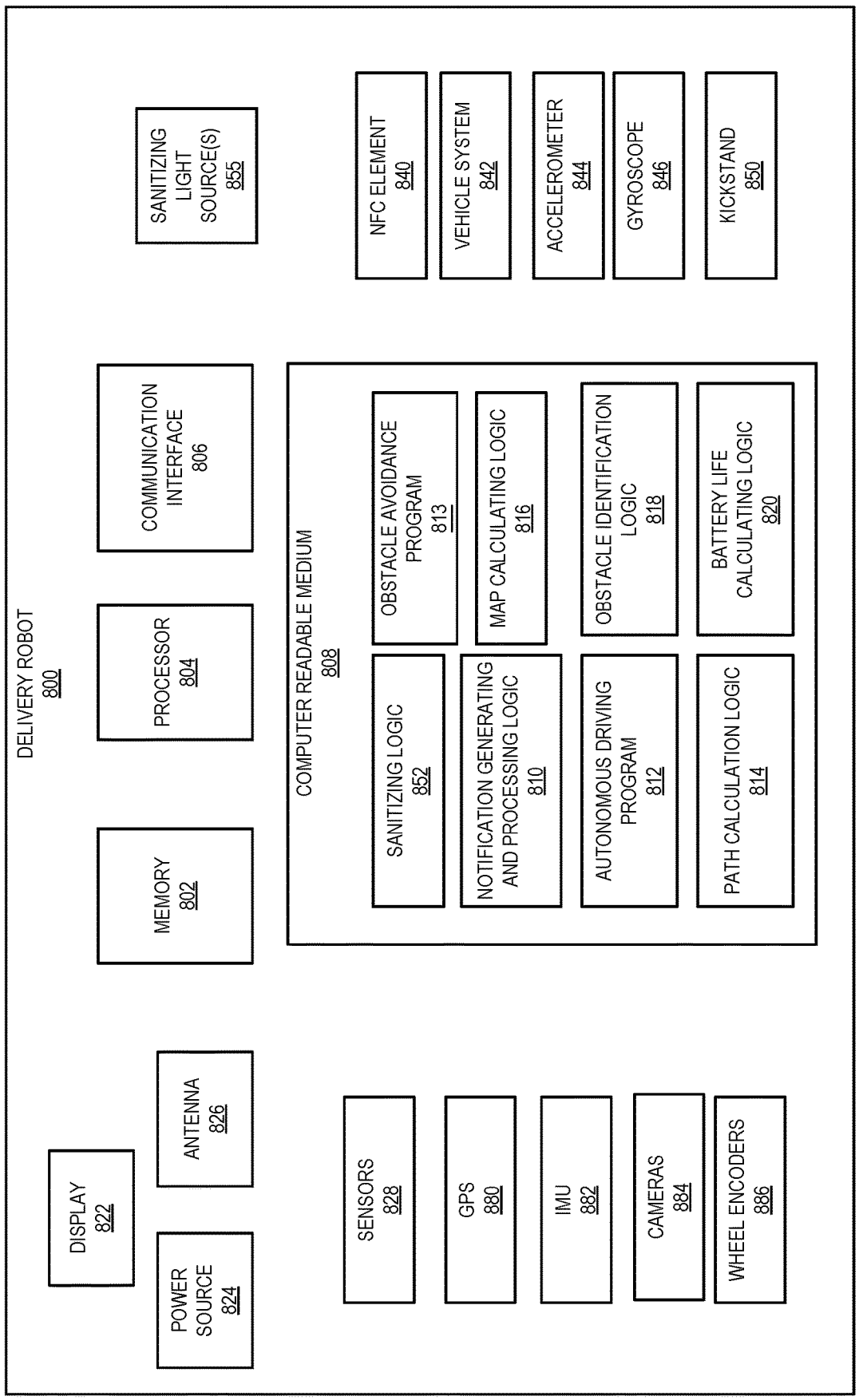
FIG. 8 illustrates a block diagram of a delivery robot, according to some embodiments.

FIG. 8 is a block diagram illustrating an example of a delivery robot 800 according to an embodiment of the disclosure. In one example, the delivery robot 800 may include one or more of a display 822, a power source 824 (e.g., a battery) for allowing the delivery robot 800 to self-drive, one or more sensors 828 (e.g., LIDAR (e.g., Light Detection And Ranging) sensors, ultrasonic range sensors, bump sensors), one or more cameras 884 (e.g., computer vision cameras, stereo-cameras, depth cameras), a global positioning system (GPS) transmitter/receiver 880, an inertial measurement unit (IMU) 882 (capable of measuring force, angular rate, and orientation of the delivery robot), accelerometer 844, gyroscope 846, wheel encoders 886, an antenna 826 to communicate with the GPS or other computer systems, and one or more sanitizing light sources among other mechanical components. For example, the delivery robot 800 may include a set of components collectively referred as a vehicle system 842. The vehicle system 842 may be associated with mechanics and power source to propel delivery robot 800 along a path, including one or more of a chassis with two, four, or six wheels, etc., gearbox, drivetrain, motor, controller, transmission, and the like.

The delivery robot 800 may also include a memory 802, a processor 804, a communication interface 806 and a computer readable medium 808, one or more of which in combination may be referred as a controller. The computer-readable medium may store instructions that are executable by the processor 804.

The memory 802 may be any suitable device or devices that can store electronic data. The memory 802 can be used to store data and code. The memory 802 may be coupled to the processor 804 internally or externally (e.g., cloud-based data storage), and may comprise any combination of volatile and/or non-volatile memory, such as RAM, DRAM, ROM, flash, or any other suitable memory device. A suitable memory may comprise a non-transitory computer readable medium that stores instructions that can be executed by a processor to implement a desired method. Examples of memories may comprise one or more memory chips, disk drives, etc. Such memories may operate using any suitable electrical, optical, and/or magnetic mode of operation.

The processor 804 may control the operation of the delivery robot 800 and may comprise one or more Application Specific Integrated Circuits (ASICs) or Field Programmable Gate Arrays (FPGAs). The processor 804 may include single core and/or multicore processors. The processing resources of the delivery robot 800 may be organized into one or more processing units. A processing unit may include one or more processors, one or more cores from the same or different processors, a combination of cores and processors, or other combinations of cores and processors. In some embodiments, the processor 804 may include one or more special purpose co-processors such as graphics processors, Digital Signal Processors (DSPs), or the like. In some embodiments, the processor 804 may be implemented using customized circuits.

In some embodiments, the processor 804 may execute instructions stored on the computer readable medium 808. In various embodiments, the processor 804 may execute a variety of programs or code instructions and may maintain multiple concurrently executing programs or processes. At any given time, some or all of the program code to be executed may be resident on the computer readable medium 808 including potentially on one or more storage devices. Through suitable programming, the processor 804 may provide various functionalities described herein.

According to various embodiments, the delivery robot 800 may stay upright using a kickstand 850 that, when deployed (either manually by the user or automatically via software), passively stabilizes the orientation of the delivery robot 800 using multiple points of contact such that delivery robot 800 may maneuver autonomously (or via teleoperation) without falling over. When the delivery robot 800 is manually operated by the user, the stabilizing kickstand 850 is retracted (either manually by the user or automatically via software). In some embodiments, the delivery robot may be mechanically passively stable (e.g., without requiring a kickstand). For example, the delivery robot may include devices with three or more wheels (e.g., three or more points of contact).

The communication interface 806 may include an interface that can allow the delivery robot 800 to communicate with external processors. Communication interface 806 may enable the delivery robot 800 to exchange data to and from another device (e.g., the central server, the user device). Some examples of the communication interface 806 may include a modem, a physical communication interface (such as an Ethernet card or other Communication interface Card (NIC)), a virtual communication interface, a communications port, a Personal Computer Memory Card International Association (PCMCIA) slot and card, or the like. The wireless protocols enabled by communication interface 806 may include WiFi. Data transferred via communication interface 806 may be in the form of signals which may be electrical, electromagnetic, optical, or any other signal capable of being received by the external communications interface (collectively referred to as "messages"). These messages that may comprise data or instructions may be provided between communication interface 806 and other devices via a communications path or channel. Any suitable communication path or channel may be used such as, for instance, a wire, fiber optics, a cellular link, a radio frequency (RF) link, a WAN or LAN network, the Internet, advanced data network technology, such as 8G, 4G, EDGE (enhanced data rates for global evolution), WiFi (IEEE 802.XX family standards) or other mobile communication technologies, or any combination thereof.

The computer readable medium 808 may comprise code, executable by the processor 804, to implement a method comprising receiving, from a central server via a communication interface, a notification including a target location; running an autonomous driving program 812 to reach the target location using a predetermined path; identifying one or more obstacles on the predetermined path in real time (for example using an obstacle identification logic 818); running an obstacle avoidance program 813 to avoid the one or more obstacles on the predetermined path, wherein the obstacle avoidance program 813 implements one or more modifications to the predetermined path; and auto-driving (for example by executing the autonomous driving program 812) to reach the target location. According to various embodiments, the target location may be located at an area closed to vehicular traffic. That is, the target location may be located on a sidewalk or on a designated route which is closed to road vehicles such as automobiles, buses, trucks, etc. Similarly, the predetermined path travels through an area closed to vehicular traffic. That is, the predetermined path travels through one or more of a sidewalk or a designated route which is closed to road vehicles such as automobiles, buses, trucks, etc. In some embodiments, the predetermined path may include a road segment shared with other motorized vehicles.

According to various embodiments, the one or more modifications to the predetermined path may be within one or more predetermined thresholds for time (e.g., remaining battery charge time, time to the target location, time to the destination), distance (e.g., distance to the target location), or speed (e.g., of the delivery robot or the dynamic obstacle). For example, the autonomous driving program 812 may be configured to operate the vehicle system 842 of the delivery robot 800 according to the predetermined path. The autonomous driving program 812 may identify a direction for the delivery robot 800 (e.g., proceed northeast, rotate 85 degrees and proceed forward) and provide instructions for moving substantially in the identified direction to the vehicle system 842. The instructions may initiate movement with the chassis, wheels, and other components of the delivery robot 800 to operate delivery robot 800 in the direction identified.

In some embodiments, the delivery robot 800 may calculate for example using map calculating logic 816) the path to the target location (e.g., the predetermined path). In such embodiments, the method may also comprise calculating (for example using battery life calculating logic 820) remaining charge of a power source 824; and calculating (for example using the path calculating logic 814) the predetermined path to the target location based on at least the remaining charge.

According to various embodiments, the delivery robot 800, upon arriving at the target location indicated by the user, may receive a user identifier of the user (for example via a near-field communication element 840). The delivery robot 800 may compare the user identifier received from the user with the user identifying information received from the central server. If the user identifier received from the user matches with the user identifying information received from the central server, the delivery robot 800 may switch control (of the delivery robot) to the user.

In some embodiments, the obstacle identification logic 818, when executed by the processor 804 may classify the one or more obstacles as dynamic obstacles such as other road users (e.g., pedestrians, bicyclist, animals, cars) or static obstacles (e.g., walls, poles, parking meters). For those obstacles classified as dynamic, the obstacle identification logic 818, when executed by the processor 804, may estimate a trajectory. The obstacle avoidance program 813, when executed by the processor 804, may help the delivery robot 800 to avoid the dynamic obstacles on the predetermined path based on the estimated trajectory of the dynamic objects.

According to various embodiments, the delivery robot 800 may include a notification generating and processing logic 810 that may process the notifications received from the central server or the user device, and may generate notifications (e.g., an acknowledgement message) that may be transmitted to the central server and/or the user device. For example, the delivery robot 800 may be parked at a parking station when the delivery robot 800 receives the notification including the target location from the central server. The delivery robot 800 may generate and transmit the acknowledgement message to the central server and detach itself from the parking station to self-drive itself to the target location indicated in the notification.

In some embodiments, the computer readable medium 808 may include a sanitizing logic 852 that, in combination with the processor 804, may run a sanitizing cycle to disinfect the cargo bin and/or the cargo provided therein. In some embodiments, the computer readable medium 808 may include a sanitizing logic 852 that, in combination with the processor 804, may activate one or more sanitizing light sources 855 to disinfect an interior of a cargo bin of the delivery robot 800. The sanitizing logic 852 may detect that a door of the cargo bin is in a closed state, and may activate one or more sanitizing (e.g., disinfecting) light sources to irradiate sanitizing (e.g., disinfecting) radiation toward and interior of the cargo bin. In some embodiments, the sanitizing logic 852 may activate the one or more sanitizing (e.g., disinfecting) light sources for a predetermined amount. In some embodiments, the sanitizing light sources 855 may include an ozone creating vacuum-UV light source. The sanitizing logic 852 may activate the ozone creating vacuum-UV light source at a predetermined time during a sanitizing cycle (and for a predetermined amount of time) to release ozone in addition to the disinfecting radiation toward the interior of the cargo bin upon detecting that the door is in a closed state.

The use of the terms "a" and "an" and "the" and similar referents in the context of describing the disclosed examples (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted.

The methods described herein can be performed in any suitable order unless otherwise indicated herein or otherwise clearly contradicted by context. The use of any and all examples, or exemplary language (e.g., "such as") provided herein, is intended merely to better illuminate examples of the disclosure and does not pose a limitation on the scope of the disclosure unless otherwise claimed. No language in the specification should be construed as indicating any non-claimed element as essential to the practice of the disclosure.

Disjunctive language such as the phrase "at least one of X, Y, or Z," unless specifically stated otherwise, is intended to be understood within the context as used in general to present that an item, term, etc., may be either X, Y, or Z, or any combination thereof (e.g., X, Y, and/or Z). Thus, such disjunctive language is not generally intended to, and should not, imply that certain examples require at least one of X, at least one of Y, or at least one of Z to each be present.

Various examples of this disclosure are described herein. Variations of those examples may become apparent to those of ordinary skill in the art upon reading the foregoing description. Any combination of the above-described elements in all possible variations thereof is encompassed by the disclosure unless otherwise indicated herein or otherwise clearly contradicted by context.

What is claimed is:

1. A delivery robot comprising:
    a cargo bin;
    a door coupled to the cargo bin, wherein the door has an open state to allow access to an interior of the cargo bin, and a closed state to seal the interior of the cargo bin from an exterior environment; and
    a disinfecting light source operable to generate a disinfecting radiation to disinfect the interior of the cargo bin, wherein the disinfecting light source is allowed to be activated when the door is in the closed state, and is prevented from being activated when the door is in the open state,
    wherein the delivery robot is programmed to navigate a delivery route to a destination, and
    wherein a controller of the delivery robot is configured to activate the disinfecting light source for a first duration of time after departing the destination.

2. The delivery robot of claim 1, wherein the interior of the cargo bin includes a reflective surface to reflect the disinfecting radiation toward a portion of the interior of the cargo bin.

3. The delivery robot of claim 1, wherein the interior of the cargo bin includes a transmissive surface to transmit the disinfecting radiation toward a portion of the interior of the cargo bin.

4. The delivery robot of claim 1, wherein the door is arranged on a topside of the cargo bin, and the disinfecting light source is mounted on an inside surface of the door.

5. The delivery robot of claim 1, wherein the disinfecting light source has a circular loop shape.

6. The delivery robot of claim 1, wherein the disinfecting light source has a linear shape.

7. The delivery robot of claim 1, wherein a controller of the delivery robot is configured to activate the disinfecting light source for a second duration of time before arriving at the destination.

8. The delivery robot of claim 7, wherein the controller is configured to keep the disinfecting light source activated for a third duration of time once the delivery robot has arrived at the destination.

9. The delivery robot of claim 8, wherein the third duration of time is less than the second duration of time.

10. The delivery robot of claim 7, wherein the destination is a cargo pickup location, and the first duration of time is longer than the second duration of time.

11. The delivery robot of claim 7, wherein the destination is a cargo drop-off location, and the first duration of time is shorter than the second duration of time.

12. The delivery robot of claim 1, wherein the disinfecting light source includes an ultraviolet light-emitting diode (UV LED).

13. The delivery robot of claim 1, wherein the disinfecting light source includes an ozone creating vacuum-ultraviolet light source that generates ozone.

14. The delivery robot of claim 13, further comprising a fan operable to circulate the ozone in the cargo bin.

15. A computer-implemented method comprising:
    initiating a delivery robot having a cargo bin to traverse a delivery route to a destination;

activating a disinfecting light source integrated with the delivery robot for a first duration of time to disinfect an interior of the cargo bin prior to arriving at the destination;

determining that the delivery robot has arrived at the destination;

in response to determining that the delivery robot has arrived at the destination, deactivating the disinfecting light source while the delivery robot is stopped at the destination;

determining that the delivery robot has departed the destination; and in response to determining that the delivery robot has departed the destination, reactivating the disinfecting light source to disinfect the interior of the cargo bin for a second duration of time.

16. The computer-implemented method of claim 15, wherein the destination is a cargo pickup location, and the second duration of time is shorter than the first duration of time.

17. The computer-implemented method of claim 15, wherein the destination is a cargo drop-off location, and the second duration of time is longer than the first duration of time.

18. The computer-implemented method of claim 15, further comprising displaying an indicator on an exterior of the delivery robot to indicate whether the disinfecting light source is activated.

* * * * *